United States Patent [19]

Piccardi et al.

[11] 4,229,470

[45] Oct. 21, 1980

[54] COMPOUNDS HAVING A TRICHLOROMETHYLIC END GROUP HAVING A JUVENILE HORMONE ACTION ON INSECTS AND ACARICIDE ACTIVITY

[75] Inventors: Paolo Piccardi; Angelo Longoni, both of Milan, Italy

[73] Assignee: Montedison S.p.A., Milan, Italy

[21] Appl. No.: 4,263

[22] Filed: Jan. 17, 1979

Related U.S. Application Data

[62] Division of Ser. No. 731,047, Oct. 8, 1976, Pat. No. 4,140,794.

[30] Foreign Application Priority Data

Oct. 9, 1975 [IT] Italy ............................... 28116 A/75

[51] Int. Cl.² ..................... A01N 9/20; A01N 9/24; C07C 43/28; C07C 121/75

[52] U.S. Cl. ..................... 424/304; 260/465 F; 260/465 G; 260/574; 260/575; 260/577; 260/578; 424/308; 424/330; 424/331; 424/337; 424/341; 560/18; 560/65; 568/642; 568/649; 568/655; 568/656; 568/44; 568/52; 568/54; 568/56; 568/337; 568/393; 568/394

[58] Field of Search ............... 260/465 F, 465 G, 574, 260/575, 609 F, 592; 560/65, 18; 568/642, 649, 655, 656; 424/304, 308, 330, 331, 337, 340, 341

[56] References Cited

U.S. PATENT DOCUMENTS

| | | | |
|---|---|---|---|
| 3,755,411 | 8/1973 | Henrick et al. | 260/465 F X |
| 3,944,531 | 3/1976 | Chodnekar et al. | 260/465 F X |
| 4,000,312 | 12/1976 | Piccardi et al. | 424/282 |

Primary Examiner—Dolph H. Torrence

[57] ABSTRACT

Compounds are disclosed which have a juvenile hormone action on insects and also exhibit acaricide action. Said compounds are unsaturated aliphatic compounds having a trichloromethyl end group and the other end group of which is a phenol group which may be substituted and/or condensed, and which are capable of hindering the growth of insects from the larval to the adult stage and also exhibit an acaricide action on both adult acari and their eggs.

13 Claims, No Drawings

COMPOUNDS HAVING A TRICHLOROMETHYLIC END GROUP HAVING A JUVENILE HORMONE ACTION ON INSECTS AND ACARICIDE ACTIVITY

This is a division of application Ser. No. 731,047 filed Oct. 8, 1976, now U.S. Pat. No. 4,140,794.

THE PRIOR ART

Application Ser. No. 540,167 filed Jan. 10, 1975, Pat. No. 4,000,312 (corresponding to Italian applications Nos. 19,332 A/74 and 28,583 A/74) discloses unsaturated aliphatic compounds having a vinyl dichloro- or trichloro-substituted end group of the general formula

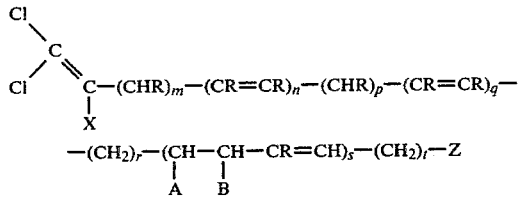

wherein:
X is H or Cl;
m, n, p, q, r, s, is 0; 1; or 2;
R which may be the same or different represent H, lower alkyls possibly branched and/or substituted;
A, B is H or A+B represents a further bond;
Z is $OR^1$; $-SR^1$; $-SOR^1$; $-C\equiv N$; or $$-N\diagup^{R_2}_{\diagdown R_3} \;;$$

—CO—Y
wherein:
$R^1$ is alkyl or lower alkenyl possibly branched and/or substituted, or $-C_6H_4W_\mu$ wherein $\mu$ is 1; 2; or 3 and W=H, halogen, lower alkyl like $R^1$, alkoxyl, thioalkyl, carbalkyl, carboxyalkyl, $-NO_2$, phenyl, a heterocyclic nucleus possibly condensed at the benzenic ring in 3, 4; or an aminic group possibly substituted with substituents forming open or closed chains in a cycle with nitrogen;
$R^2$, $R^3$, the same or different represent H, possibly substituted lower alkyls, or $R^2+R^3$ forms with N and/or additional heteroatoms, a cycle of 5, 6, or 7 atoms; and
Y is H, lower alkyl, lower alkoxyl, —OH, —O-metal, cycloalkyl or aryl.

Said compounds display a good juvenile hormone activity (such, that is, to inhibit the growth of the insects from the larval to adult stage). However, because the dichloro- or trichloro-vinyl end group, often near other unsaturated groups, tends to be unstable, those compounds may be difficult to use under particular conditions.

THE PRESENT INVENTION

We have now found, and this is one object of the present invention, that compounds having a trichloromethyl end group and of the general formula:

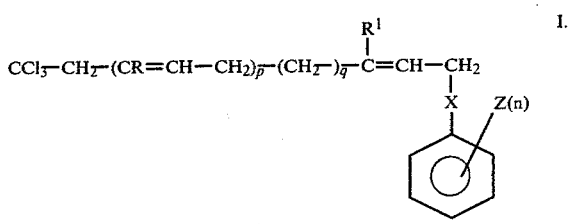

wherein:
R is H or $CH_3$;
$R^1$ is $CH_3$ or $C_2H_5$;
p is 0 or 1;
q is 1 or 2 (when p=1, q must be 1);
X is O or S;
n is 1, 2 or 3;
Z is H, halogen, alkyl with from 1 to 5 carbon atoms; alkoxyl with $C_1$-$C_5$; thioalkyl with $C_1$-$C_5$; carboalkyl with $C_1$-$C_5$; carboxyalkyl with $C_1$-$C_5$; $NO_2$; phenyl; a condensed heterocyclic nucleus with a benzoic ring;

wherein $R^2$ and $R^3$, the same or different, are H or an alkyl with $C_1$ to $C_5$; CN; are possessed of both good juvenile hormone activity and acaricide effectiveness.

The method of preparing the present compounds, which is also a feature of this invention, involves reactions which are partly known and which start from materials of petrochemical origin that are widely available.

The first series of reactions has the object of preparing ketones of the general formula:

(wherein R, $R^1$, p and q have the same values as in formula I). The schemes are the following:

(1st)

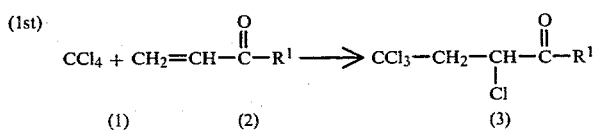

(1)     (2)     (3)

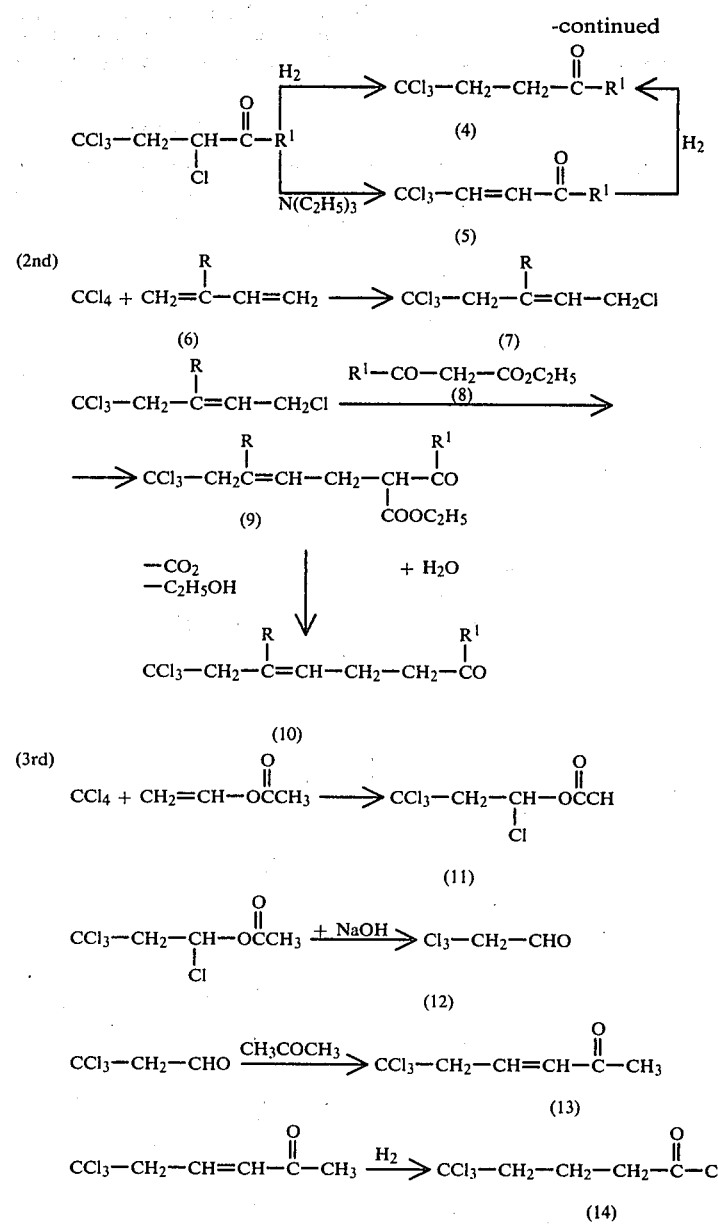

According to the 1st scheme, the condensation reaction is carried out between carbon tetrachloride and an alkyl-vinyl-ketone according to a Redox-reaction of the type described by Vofsi & Ascher in the Journal Chemical Society 1963, 3921. Thereby aduct (3) is obtained which may be hydrogenated to the saturated ketone (4), or dehydrohalogenated to the unsaturated α-β ketone (5), in its turn hydrogenatable to (4).

According to the 2nd scheme, the carbon tetrachloride is added to a 1,3-diene (6) in order to obtain the aduct (7); this latter, condensed with the β-ketoester (8), gives the intermediate (9) which, by a successive hydrolytic decarbooxylation, supplies the γ,β-unsaturated ketone (10).

According to the 3rd scheme, the carbon tetrachloride is condensed with vinyl acetate to obtain the intermediate (11), which latter, by alkaline hydrolysis, is converted to aldehyde (12). The crotonic type condensation of the aldehyde with acetone yields with α,β-unsaturated ketone (13) which, by hydrogenation, may be converted to the saturated ketone (14).

The compounds of formula (I) are obtained from the $$CCl_3-CH_2-(CR=CH-CH_2)_p-(CH_2)_q-\overset{O}{\underset{\|}{C}}-R^1$$ ketones by the following steps:

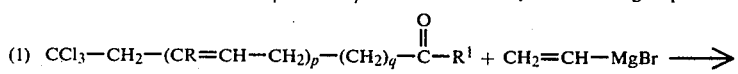

-continued

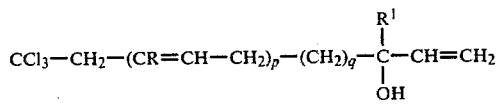

(15)

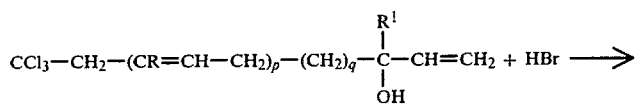

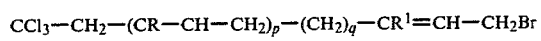

(16)

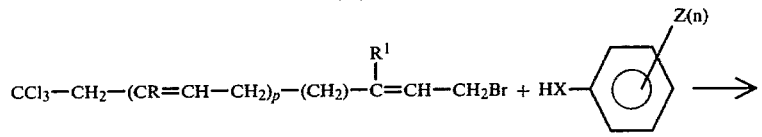

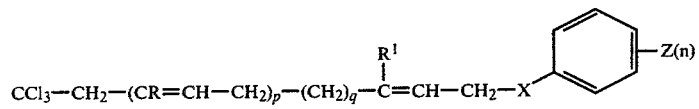

(17)

(2) The unsaturated alcohol 15 may also be obtained by reacting the starting ketone with alkaline acetylide:

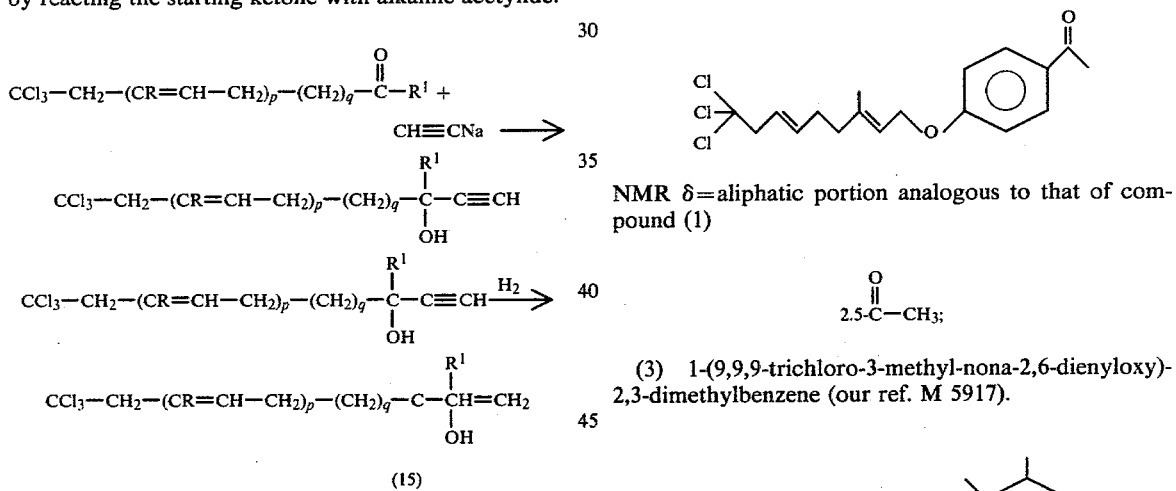

(15)

The products (16) and (17) are then obtained as shown above.

Among others, there have been prepared the following compounds of the formulae given, and which are further identified by our reference number, the NMR spectrum and, in some instances, other characteristics:

(1) 4-(9,9,9-trichloro-3-methyl-nona-2,6-dienyloxy)-tert.-butylbenzene (our reference M 5915).

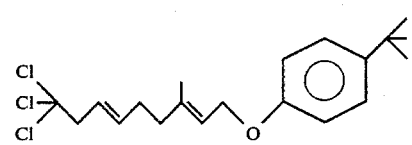

NMR $\delta = 1.25$ 3—$CH_3$; 1.78 —$CH_3$; 2.24 —$CH_2$—$CH_2$; 3.25 $CCl_3$—$CH_2$; 4.60 —$CH_2$—O; 5.55, 3 vinylic H; 6.7–7.3, 4 aromatic H in p.p.m.

(2) 4-(9,9,9-trichloro-3-methyl-nona-2,6-dienyloxy)-acetophenone (our ref. M 5916).

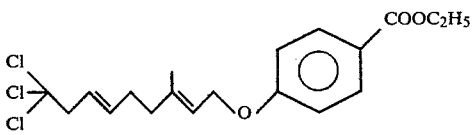

NMR $\delta$ =aliphatic portion analogous to that of compound (1)

$2.5\text{-}\overset{\text{O}}{\underset{\|}{C}}\text{—}CH_3$;

(3) 1-(9,9,9-trichloro-3-methyl-nona-2,6-dienyloxy)-2,3-dimethylbenzene (our ref. M 5917).

NMR $\delta$ =aliphatic portion analogous to that of compound (1)

(4) 4-(9,9,9-trichloro-3-methyl-nona-2,6-dienyloxy)-ethyl benzoate (our ref. M 5918).

NMR $\delta$ =aliphatic part analogous to that of compound (1); 1.45 —$CH_2$—$CH_3$; 4.49 —O—$CH_2$; 7.0–8.05, 4 aromatic H.

(5) 1-(9,9,9-trichloro-3-methyl-nona-2,6-dienyloxy)-3,5-dimethylbenzene (our ref. M 5919).

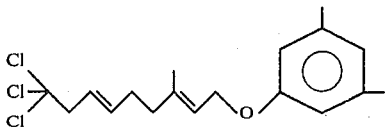

NMR δ=aliphatic portion analogous to that of compound (1); 2.18, 2CH₃, 6.35–6.45, 3 aromatic H.

(6) 1-(9,9,9-trichloro-3-methyl-nona-2,6-dienyloxy)-3,4-dimethylbenzene (our ref. 5920).

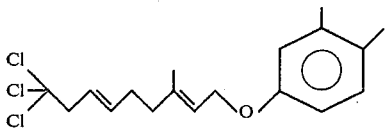

NMR δ=aliphatic portion analogous to that of compound (1);

(7) 4-(9,9,9-trichloro-3-methyl-nona-2,6-dienyloxy)-methylbenzoate (our ref. M 5921).

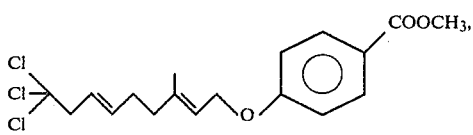

NMR δ=aliphatic portion analogous to that of compound (1); 4.05 —OCH₃; 7.0–8.05, 4 aromatic H.

(8) 3-(9,9,9-trichloro-3-methyl-nona-2,6-dienyloxy)-methylbenzene (our ref. M 5923).

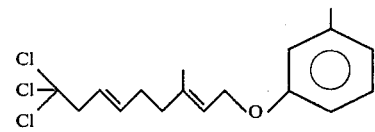

NMR δ=aliphatic portion analogous to that of compound (1); 2.25 CH₃; 6.60–7, 4 aromatic H.

(9) 3-(9,9,9-trichloro-3-methyl-nona-2,6-dienyloxy)-methoxybenzene (our ref. M 5924).

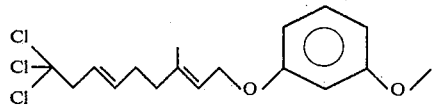

NMR δ=aliphatic portion analogous to that of compound (1); 3.75 OCH₃, 6.5–7.30, 4 aromatic H.

(10) 3-(9,9,9-trichloro-3-methyl-nona-2,6-dienyloxy)-nitrobenzene (our ref. M 5925).

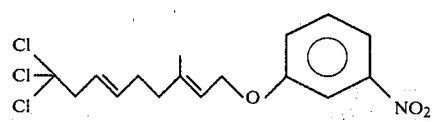

NMR δ=aliphatic portion analogous to that of compound (1) 7.20–7.60, 4 aromatic H.

(11) 4-(9,9,9-trichloro-3-methyl-nona-2,6-dienyloxy)-methylthiobenzene (our ref. M 5926).

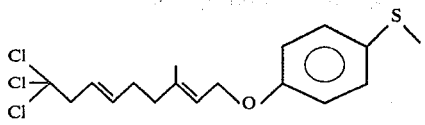

NMR δ=aliphatic portion analogous to that of compound (1); 2.42, S—CH₃; 6.75–7.22, 4 aromatic H.

(12) 1-(9,9,9-trichloro-3,7-dimethyl-nona-2,6-dienyloxy)-3,4-methylendioxybenzene (our ref. M 6239).

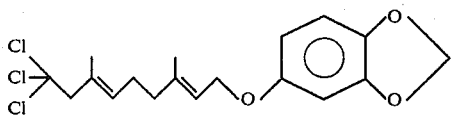

NMR δ=1.75, —CH₃; 1.88, —CH₃; 2.23, —CH₂—; 3.35 CCl₃—CH₅; 4.60, CH₂—O—; 5.5, 2H; 5.80, —O—CH₂—O; 6.15–6.7, 3 aromatic H.

(13) 4-(9,9,9-trichloro-3,7-dimethyl-nona-2,6-dienyloxy)-ethylbenzene (our ref. M 6241).

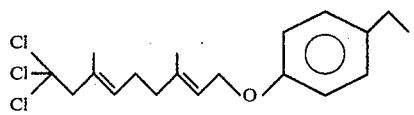

NMR δ=aliphatic portion analogous to that of compound (12); 1.19, CH₂—CH₃; 2.58, —CH₂—CH₃; 6.75–7.05, 4 aromatic H.

(14) 4-(9,9,9-trichloro-3,7-dimethyl-nona-2,6-dienyloxy)-acetophenone (our ref. M 6242).

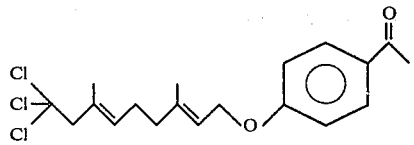

NMR δ=aliphatic portion analogous to that of compound (12); 2.50, O—CH₃; 6.80–7.80, 4 aromatic H.

(15) 4-(9,9,9-trichloro-3,7-dimethyl-nona-2,6-dienyloxy)-isopropylbenzene (our ref. M 6243).

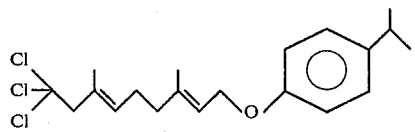

NMR δ=aliphatic portion analogous to that of compound (12); 1.20, 2CH₃; 2 8, —CH(CH₃)₂; 6.80–7.05, 4 aromatic H.

(16) 4-(9,9,9-trichloro-3,7-dimethyl-nona-2,6-dienyloxy)-n.propylbenzene (our ref. M 6244).

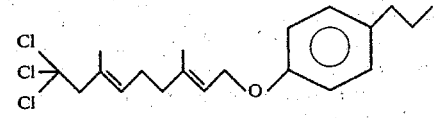

NMR δ=aliphatic portion analogous to that of compound (12); 0.70, CH₃; 1.55, CH₂—CH₃; 2.5, —CH₂—CH₂—CH₃; 6.7-6.9, 4 aromatic H.

(17) 4-(9,9,9-trichloro-3,7-dimethyl-nona-2,6-dienyloxy)-methylbenzene (our ref. M 6245).

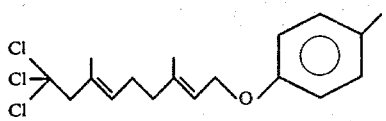

NMR δ=aliphatic portion analogous to that of compound (12); 2.30, —CH₃; 6.75-7.1, 4 aromatic H.

(18) 4-(9,9,9-trichloro-3.7-dimethyl-noma-2,6-dienyloxy)-methoxybenzene (our ref. M 6246).

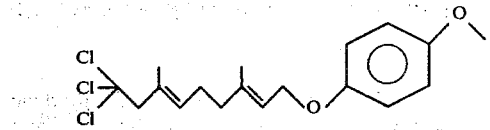

NMR δ=aliphatic portion analogous to that of compound (12); 3.65, —O—CH₃; 6.60, 4 aromatic H.

(19) 4-(9,9,9-trichloro-3,7-dimethyl-nona-2,6-dienyloxy)-thiomethylbenzene (our ref. M 6248).

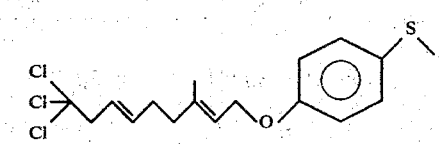

NMR δ=aliphatic portion analogous to that of compound (12); 2.40, —S—CH₃; 6.75-7.20, 4 aromatic H.

(20) 4-(9,9,9-trichloro-3,7-dimethyl-nona-2,6-dienyloxy)-nitrobenzene (our ref. M 6249).

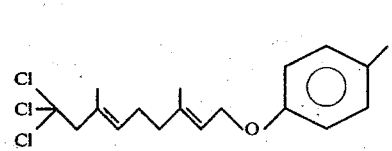

NMR δ=aliphatic portion analogous to that of compound (12);

(21) 3-(9,9,9-trichloro-3,7-dimethyl-nona-2,6-dienyloxy)-anisole (our ref. JH 22).

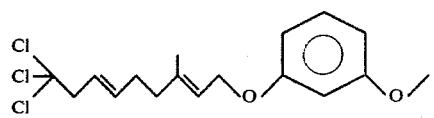

NMR δ=aliphatic portion analogous to that of compound (12); 3.75, —O—CH₃; 6.50-7.30, 4 aromatic H.

(22) 2-(9,9,9-trichloro-3,7-dimethyl-nona-2,6-dienyloxy)-5-tert.-butyl-chlorobenzene (our ref. JH 12)

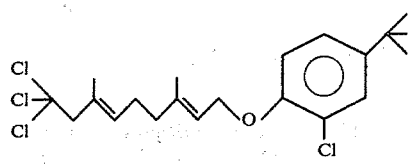

NMR δ=aliphatic portion analogous to that of compound (12); 1.31 3—CH₃; 6.70-7.40, 3 aromatic H Elementary analysis: C=5.72 (57.5); H=6.5 (6.38); Cl=31.5 (32.4)%.

(23) 3-(9,9,9-trichloro-3,7-dimethyl-nona-2,6-dienyloxy)-benzonitrile (our ref. JH 8).

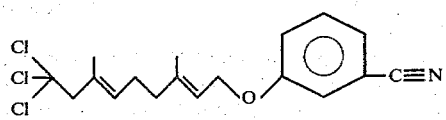

NMR δ=aliphatic portion analogous to that of compound (12); 7.30, aromatic 4H elementary analysis: C=57.5 (58.04); H=5.35 (5.38); Cl=27 (28.6)%.

(24) 3-(9,9,9-trichloro-3,7-dimethyl-nona-2,6-dienyloxy)-acetophenone (our ref. JH 4).

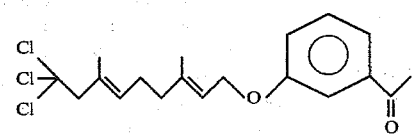

NMR δ=aliphatic portion analogous to that of compound (12); 2.54 —CO—CH₃; 7.0-7.5, 4 aromatic H Elementary analysis: C=59.0 (58.54); H=5.9 (5.90); Cl=26.5 (27.34)%.

(25) 3-(9,9,9-trichloro-3,7-dimethyl-nona-2,6-dienyloxy-ethylbenzene (our ref. JH 7)

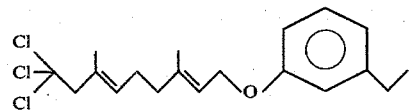

NMR δ=aliphatic portion analogous to that of compound (12); 1.24, —CH₂—CH₃; 2.65, —HC₂—CH₃; 6.75-7.38, 4 aromatic H. Elementary analysis: C=61.0 (60.72); H=6.8 (6.66); Cl=26.7 (28.36).

(26) 4-(9,9,9-trichloro-3,7-dimethyl-nona-2,6-dienyloxy)-ethylbenzoate (our ref. JH 5):

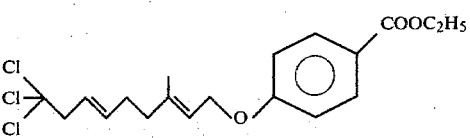

NMR δ=aliphatic portion analogous to that of compound (12); 1.38 —OCH₂—CH₃; 4.50 —OCH₂—CH₃; 6.9-5-8.07, 4 aromatic H

(27) 4(9,9,9-trichloro-3,7-dimethyl-nona-2,6-dienyloxy)-benzonitrile

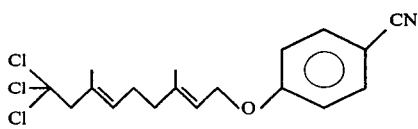

NMR δ=aliphatic portion analogous to that of compound (12); 7.01–7.61, 4 aromatic H Elementary analysis: C=57.5 (57.98), H=5.4 (5.37), N=3.7 (3.76), Cl=27.7 (28.6).

The activity of compounds (1) to (27) varies according to the compound and to the species on which they have been tested, as do others of the same series and comprised within this invention. Thus, for instance, the compound identified by us as JH 8 has a good juvenile hormone activity at 200 γ/insect on *Spodoptera littoralis*, while its activity is null at the same concentrations on *Tenebrio molitor*.

On the contrary, compound M 6249 is highly active at concentrations of 20 γ/insect on *Tenebrio molitor*, while it is inactive at 200 γ/insect on *Spodoptera littoralis*.

Also the acaricide activity varies from compound to compound and, depending on whether tested on adult insects or on the eggs.

Compound M 5918, for instance, shows a certain acaricide activity at a concentration of 0.1% on the eggs of *Tetranichus urticae*, while it is inactive at the same concentrations on the adult insect. On the contrary, compound M 5926 is more active on the adult insect than on the eggs at the same concentrations.

The hormone juvenile activity has been tested, under the conditions described in Example 13, on the following species: *Tenebrio molitor, Pieris brassicae, Spodoptera littoralis*, for topical treatment on pupae and larvae; *Anagasta kueniella, Tribolium confusum, Aedes aegypti* for the treatment of the habitat or of the substrate on which the larvae were growing. For *Musca domestica*, the active principle was applied on the adults and there were then ascertained, after given periods of time, the effects on the undisclosed eggs, the larvae that had become pupae, and then the born adults.

The acaricide activity was tested on *Tetranychus urticae*, both on the adult insect as well as on the eggs, as described in Example 14.

The following examples are given to better illustrate this invention, and are not intended as limiting.

EXAMPLE 1

Preparation of mixture (E)-1,5,5,5-tetrachloro-2-methyl-pent-2-ene, and (E)-1,5,5,5-tetrachloro-3-methyl-pent-2-ene.

Reaction:

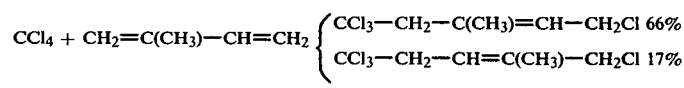

Into a stainless steel 500 ml autoclave was loaded a mixture of CCl₄ (153 g, 1 mol), isoprene (34.1 g—0.5 mol), CH₃—CN (39 g—0.94 mol), CuCl₂.2H₂O (0.85 g) and n-butylamine (0.875 g).

After 6 hours at 130° C., the autoclave was cooled down and the content was recovered. From two identical tests there were obtained 433 g of a dark oil which, after concentration at reduced pressure, washed with water and drying, yielded 213 g of a mixture containing 17% by weight of (E)-1,5,5,5-tetrachloro-2-methyl-pent-2-ene and 66% b.w. of (E)-1,5,5,5-tetrachloro-3-methyl-pent-2-ene, this mixture having a boiling point of 116°–118° C. at 20 mm Hg.

The separation of the two isomers was carried out by gas chromatography and the identification was established through the NMR spectrum (Nuclear Magnetic Refraction).

EXAMPLE 2

Preparation of (E)-2-acetyl-7,7,7-trichloro-5-methyl-ept-4-ethyl enoate (Scheme A).

Reaction:

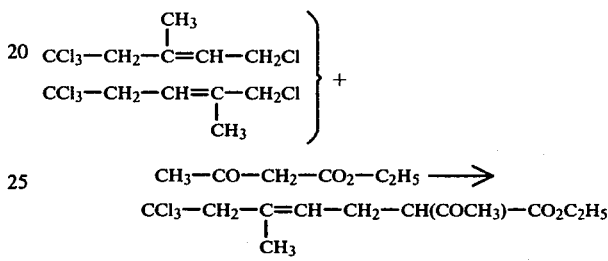

Into a 1 lt flask were loaded 250 ml of anhydrous tetrahydrofurane, 9.8 g (0.224 mol) of NaH in a 55% b.w. mixture in mineral oil.

Under gentle stirring and being careful not to exceed 33° C., there were introduced into the autoclave 292 g (0.224 mol) of ethyl acetoacetate, and then 55 g of the mixture of isomers of Example 1 (respectively 0.0867 mol and 0.161 mol). The resulting mass was refluxed for 8 hours and was then left to rest at room temperature for 12 hours.

The tetrahydrofurane was then evaporated at reduced pressure and the residue was poured into water. An organic phase separated and was combined with the extracts from the water with CH₂Cl₂. After drying the extracts in organic solvent on NaSO₄ and after evaporation under vacuum, there was obtained, by distillation under vacuum of the residue, an oil (42 g, 0.133 mol) consisting of (E)-2-acetyl-7,7,7-trichloro-5-methyl-ept-4-ethyl eonate having a b.p. of 108°–110° C. at 0.001 mm Hg.

The product, purified by gas chromatography, was identified on the basis of the NMR spectrum.

EXAMPLE 3

Preparation of (E)-8,8,8-trichloro-6-methyl-oct-5-en-2-one.

Reaction:

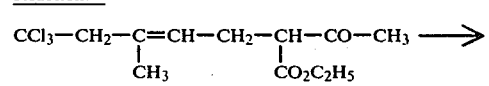

-continued $$CCl_3-CH_2-\underset{\underset{CH_3}{|}}{C}=CH-CH_2-CH_2COCH_3$$

37.5 g (0.119 mol) of 2-acetyl-7,7,7-trichloro-5-methyl-hept-4-ethyl enoate were added dropwise into a solution of 7.8 g of 85% KOH in 100 ml of H$_2$O. This mixture was then subjected to stirring at room temperature until dissolution of the ester (about 4 hours), and then extracted with ethyl ether to remove the unreacted ester.

The aqueous phase was then acidified with 30 g of H$_2$SO$_4$ at 50% concentration, refluxed for 1 hour and, after cooling down, extracted with ether.

The ether extracts, after washing with water and drying on anhydrous Na$_2$SO$_4$, were evaporated under vacuum. The residue, distilled under vacuum, gave an oil (11.6 g, 0.0475 mol) with a b.p. of 70°–72° C. at 0.1 mm Hg, besides 22.6 g of unreacted ketoester. The oil, after purification by gas chromatography, was identified as (E)-8,8,8-trichloro-6-methyl-octo-5-en-2-one on the basis of the NMR spectrum.

EXAMPLE 4

Preparation of 9,9,9-trichloro-3,7-dimethyl-nona-1,6-diene-3-ole.

$$CCl_3-CH_2-C(CH_3)=CH-CH_2-CH_2-CO-CH_3 +$$
$$CH_2=CH-MgBr \longrightarrow$$
$$CCl_3-CH_2-C(CH_3)=CH-CH_2-CH_2-\underset{\underset{OH}{|}}{C(CH_3)}-CH=CH_2$$

Into a 2,000 ml flask were introduced 33 g of magnesium shavings which were covered with 360 ml of anhydrous tetrahydrofurane. Under stirring and in a nitrogen atmosphere, there were added dropwise 127 g of vinyl bromide in 320 ml of anhydrous tetrahydrofurane, so that the temperature did not exceed 40°–50° C.

Once the addition had been completed, the mass was reflux-heated for 30 minutes; thereupon the temperature was brought down to room temperature and into it was introduced dropwise a solution of 286 g of (E)-8,8,8-trichloro-6-methyl-oct-5-en-2-one in 220 ml of anhydrous tetrahydrofurane, taking care not to exceed 30° C. After the operation had been accomplished, the reaction mixture was left to rest at room temperature for 24 hours. After this the reaction mixture was hydrolyzed with ice and ammonium chloride. Then it was decanted, extracted with ethyl ether, and the extract was washed with water and dried on anhydrous Na$_2$SO$_4$.

After evaporation of the solvent and distillation, there were obtained 173 g of a product boiling at 90°–95° C. at 0.001 mm Hg, and which was identified as 9,9,9-trichloro-3,7-dimethyl-nona-1,6-dien-3-ole by means of the NMR.

EXAMPLE 5

Preparation of 1-bromo-9,9,9-trichloro-3,7-dimethyl-nona-2,6-diene.

Reaction:

$$CCl_3-CH_2-C(CH_3)=CH-CH_2-CH_2-\underset{\underset{OH}{|}}{\overset{\overset{CH_3}{|}}{C}}-CH=CH_2 + HBr \longrightarrow$$
$$CCl_3-CH_2-C(CH_3)=CH-CH_2CH_2-C(CH_3)=CH-CH_2Br$$

To 194.5 g of a 48% solution of HBr in water there were added 105.2 g of the alcohol of the preceding example at 0°–5° C.

After stirring for 1 hour at 0° C., the reaction mixture was poured into water and ice and the organic layer was separated and added to the ether extract of the aqueous phase.

The mixture was then washed with a 10% b.w. aqueous solution of Na$_2$CO$_3$ and, then, with water, until reaching neutrality. Thereupon, it was dried on Na$_2$SO$_4$, the ether was evaporated under reduced pressure, and distillation was carried out under vacuum. Thereby were obtained 110 g of oil having a b.p. of 100°–105° C. at 0.05 mm Hg.

On NMR spectrography examination, said oil was found to consist of 70% b.w. of isomer 1-bromo-9,9,9-trichloro-3,7-dimethyl-nona-(E)-6-diene and of 30% b.w. of isomer 1-bromo-9,9,9-trichloro-3,7-dimethyl-nona-(Z)-2-(E)-6-diene.

EXAMPLE 6

Preparation of 1-(9,9,9-trichloro-3,7-dimethyl-nona-2,6-dienyloxy)-3,4-methylendioxybenzene (our ref. 6239).

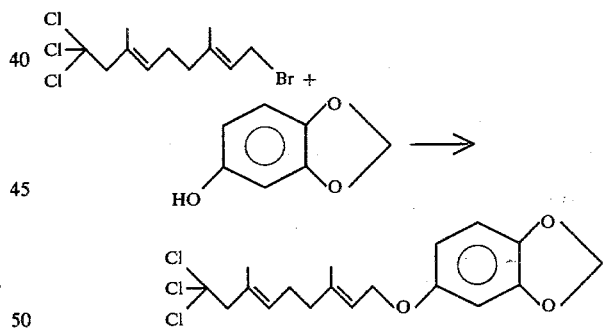

Under stirring and in an inert atmosphere, 20.6 g of 3,4-methylene-dioxy-phenol were mixed with a suspension of K$_2$CO$_3$ (20.6 g) in methylethylketone (200 cc). The mixture was cooled down to 0° C. and additioned with 50 g of the bromide of the preceding Example. The mass was then stirred for 48 hours at 0° C. after which the reaction mixture was poured over ice.

The organic residue that separated and the ether extracts of the aqueous phase, combined, were decolored with active coal, and concentrated at reduced pressure.

Thereby were obtained 60 g of 1-(9,9,9-trichloro-3,7-dimethyl-nona-2,6-dienyloxy)-3,4-methylendioxybenzene. The NMR spectrum, compatible with the structure given, was obtained on a product purified by a preparatory thin-layer chromatography (carrier: Merck silica gel; solvents: n-hexane-ethyl ether 90:10).

EXAMPLE 7

Preparation of 4,5,5,5-tetrachloro-pentan-2-one.

Into a Pfaudler ½ gallon autoclave was loaded a mixture of methylvinylketone (213 g), $CH_3CN$ (195 g), $CCl_4$ (925 g), $CuCl_2.2H_2O$ (5.1 g) and n-butylamine (5.25 g). This reaction mixture was heated for 5 hours at 120° C. under constant stirring. During this period the internal pressure of the autoclave changed from 3.5 kg/sq.cm to 3.1 kg/sq.cm. After removal, at reduced pressure, of the greatest part of the volatile substances, the residue was washed with water, reunited with the ether extracts of the aqueous phase, dried (on $Na_2SO_4$) and distilled to yield 290 g of 4,5,5,5-tetrachloro-pentan-2-one (boiling point 108°–110° C. at 18 mm Hg).

EXAMPLE 8

Preparation of 5,5,5-trichloro-pentan-2-one.

A solution of 25 g of ketone (prepared as above) in 25 ml of glacial acetic acid was added to a suspension of 12.5 g of Zn powder in 50 ml of tetrahydrofuran (THF).

The addition was carried out taking care not to exceed 30° C. After 1 hour of stirring at the reflux temperature of the THF, the reaction mixture was hydrolyzed with water. After distillation the orlgaic residue yielded 13 g of 5,5,5-trichloropentan-2-one (b.p. 83°–85° C. at 16 mm Hg).

The NMR spectrum in $CCl_4$ was $\delta = 2.185$ (3H, s, $CH_3$), 2.932 (4H, t $J \simeq 2.7$ Hz, $-CH_2-CH_2-$).

EXAMPLE 9

Preparation of 6,6,6-trichloro-3-methyl-es-1-en-3-ole.

Using the procedure described in Example 4 there were obtained, from 7 g of 5,5,5-trichloropentan-2-one, 0.9 g of Mg, 4.35 g of vinyl bromide and 75 ml of THF, 5.7 g of 6,6,6-trichloro-3-methyl-es-1-en-3-ole (b.p. 105°–107° C. at 18 mm Hg).

EXAMPLE 10

Preparation of 1-bromo-6,6,6-trichloro-3-methyl-es-2-ene.

Using the procedures of Example 5 there were obtained, from 5.7 g of 6,6,6-trichloro-3-methyl-es-1-en-3-ole, 6 g of 1-bromo-6,6,6-trichloro-3-methyl-es-2-ene.

By elementary analysis and examination of the NMR spectrum ($CCl_4$) the product was identified by the following data: $\delta = 1.7$ (s, $CH_3$ of the trans-isomer), 1.76 (s, $CH_3$ of the cis-isomer), 2.4–2.9 (4H, m, $CH_2CH_2$), 3.9 (2H, d $J \simeq 8$ Hz, $-CH_2Br$), 5.5 (1H, t $J \simeq 8$ Hz, $=CH-$).

EXAMPLE 11

Preparation of 1-(6,6,6-trichloro-3-methyl-es-2-enyloxy)-3,4-methylen-dioxybenzene.

Example 6 was repeated but using 5 g of 1-bromo-6,6,6-trichloro-3-methyl-es-2-ene. There were obtained, after separation in a column chromatography, 3 g of 1-(6,6,6-trichloro-3-methyl-es-2-enyloxy)-3,4-methylen-dioxy-benzene which by elementary analysis and examination of the NMR spectrum, was identified as follows: $[CC]_4$, $\delta = 1.8$ (3H, s, Me), 2.4–2.9 (4H, CH, $CH_2CH_2$), 4.35 (2H, s, $OCH_2O$), 6.15 (1H, dd $J \simeq 7.5$ and $J \simeq 2$ Hz, aromatic H (6)), 6.35 (1H, d $J \simeq 2$ Hz, aromatic H (2)), 6.56 (1H, d $J \simeq 7.5$ Hz, aromatic H (5))].

EXAMPLE 12

Preparation of 1-bromo-9,9,9-trichloro-3-methyl-nona-2,6-diene.

From 65 g of (E)-1,1,1-trichloro-oct-3-en-7-one, prepared as indicated by W. J. Pyne in *Journal of Organic Chemistry* 27, p. 3483, 1962, and operating as in Example 4, there were obtained 30 g of 9,9,9-trichloro-3-methyl-nona-1, 6-dien-3-ole, which when treated with an excess of 40% HBr as in Example 5, resulted in 35 g of an oil having a boiling point of 100°–102° C. at 0.05 nm Hg.

Examination of the NMR spectrum showed that said oil consisted of a mixture, in a ratio 70:30, of forms E and Z of the 1-bromo-9,9,9-trichloro-3-methyl-nona-2,6-diene.

EXAMPLE 13

Preparation of 1-(9,9,9-trichloro-3-nona-2,6-dienyloxy)-3,4-methylenedioxybenzene.

From 4 g of allyl bromide, prepared as described in the preceding example and operating with the same stoichiometric ratios and in accordance with Example 6, there were obtained 3 g of the juvenoid of the title of this example (b.p.: 138°–145° C. at 0.00] mm Hg).

EXAMPLE 14

The juvenile hormone activity of the products were tested on *Tenebrio molitor, Tribolium confusum, Pieris bassicae, Spodoptera littoralis, Aedes Aegypti, Musca domestica*.

The conditions under which the tests were conducted are reported below, species by species:

(1) *Tenbrio m.*

0–24 hour aged pupae were treated by topical application on the antepenultimate urosternite with an acetone solution of the product (2 cu. mm). The results were surveyed after about 9 days, when the insects of the witness group had completed their emergence from the cocoons.

(2) *Pieris b.*

Larvae of the last age were treated by topical application on the first urosternites with an acetone solution of the product (2 cu. mm).

Survey of the results was made about every 5 days up to the complete emergence from the cocoons of the adults in the witness group.

(3) *Spodoptera l.*

Larvae of the last age were treated by topical application on the first urosternites with an acetone solution of the product (2 cu. mm).

Survey of the results was made about every 5 days up to the complete emergence from the cocoons of the adult insects in the witness group.

(4) *Anagasta k.*

5 g of maize meal were uniformly treated with an acetone solution of the product. 24 hours after the treatment, the meal (or flour) was infested with 21 days old larvae.

The survey of the results was made every 3–4 days starting from the first appearance of the adult insects until the end of the emergence from the cocoons in the witness group.

(5) *tribolium e.*

5 g of wheat meal were uniformly treated with an acetone solution of the product. 24 hours after the treatment the flour was infested with 22 days old larvae.

Evaluation of the results was made about 45 days later, when the insects of the witness group had completed emergence from the cocoons.

(6) Musca d.

5 g of sugar and 5 g of a mixture consisting of sugar, milk and egg yolk powder were treated separately with an acetone solution of the product.

After evaporation of the solvent, the sugar and the mixture were introduced separately into two beakers together with 50 adult flies, 25 males and 25 females.

Successively, to the flies fed with the treated sugar was given the above said egg-based mixture that had not been treated, however, with the compounds of this invention. After the first egg laying, 100 eggs were transferred to the nutritive substratum (pabulum). After 2 days there was determined the percentage of disclosed eggs; after a further 5 days the pupae were gathered together and counted and 4 days later the percentage of adults which emerged from the cocoons was established.

(7) Aedes aegypti.

3 cc of an acetone solution of the product were added to 297 cc of tap water into which were successively transferred 25 larvae, four days old, and which were supplied with suitable food. The results were surveyed every 2-3 days until the end of the emergence from the cocoons of the witness group. Evaluation criteria of the activity for the insects of tests 1-4, 5 and 7.

As activity index there was adopted the percent ratio of dead individuals, misshapen and abnormal individuals with respect to the number of treated individuals, according to the following formula:

$$\text{activity} = \frac{\text{dead + misshapen + abnormal individuals}}{\text{treated individuals}} \%$$

Evaluation criteria on the results of the test on *Musca domestica* (6).

As activity index was adopted the percent ratio of the undisclosed eggs with respect to the total of eggs laid by the insects treated, using the following formula:

$$\text{activity} = \frac{\text{undisclosed eggs}}{\text{total of laid eggs}} \%$$

The results of the tests referred to herein are reported in Table I.

The conditions under which the tests were conducted are as follows:

Eggs: small discs of bean leaves were infested with acari eggs and then treated by sprinkling with an aqueous suspension of a 0.1% concentration of the product under examination. The mortality rate (untreated small leaves discs=0) is recorded in Table II.

Adults: Small discs of bean leaves were infested with acari adults and then treated with an aqueous dispersion of a 0.1% concentration of the product under examination. The death rate (untreated small discs=0) was recorded in Table II.

TABLE II

Acaricide activity on *Tetranychus urticae* adults and eggs by products of the invention at 0.1% concentration

| PRODUCT | *Tetranychus urticae* | |
|---|---|---|
|  | Adults | Eggs |
| M 6239 | 18 | 15 |
| M 6242 | 24 | 8 |
| M 6244 | 27 | 80 |
| M 5925 | 38 | 49 |
| M 5926 | 79 | 64 |
| M 5915 | 48 | 11 |
| M 5917 | 87 | 83 |
| M 5920 | 66 | 83 |

We claim:
1. Compounds of the general formula:

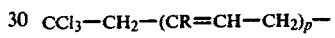
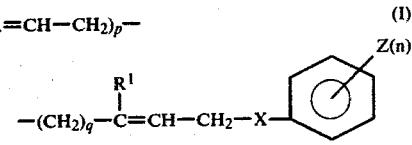

wherein:
R=H; CH$_3$
R$^1$=CH$_3$; C$_2$H$_5$
p=0; 1
q=1; 2 (when p=1, q must be 1);
X=O; S
n=1; 2; 3
Z=H; halogen; alkyl containing 1-5 carbon atoms; alkoxyl containing 1-5 carbon atoms; C$_1$-C$_5$ thioalkyl; C$_1$-C$_5$ carboalkyl; C$_1$-C$_5$ carboxyalkyl; NO$_2$; phenyl;

TABLE I

JUVENILE HORMONE ACTIVITY OF THE COMPOUNDS OF THIS INVENTION

| | Tenebrio molitor γ/ins. | | Tribolium conf. p.p.m. % | Pieris brassicae γ/ins. | Spodoptera littoralis γ/ins. | Anagasta kuehniella p.p.m. | Aedes aegypti p.p.m. | Musca domestica adults % |
|---|---|---|---|---|---|---|---|---|
| PRODUCT | 200 | 20 | 2000 | 200 | 200 | 2000 | 20 | 1 |
| M 6239 | 100 | 100 | 95 | 100 | 100 | 100 | 100 | 100 |
| M 6241 | 100 | 100 | 100 | — | 100 | 76 | 49 | 1 |
| M 6242 | 100 | 100 | 100 | 100 | 34 | 70 | 35 | 36 |
| M 6249 | 100 | 55 | 100 | — | 0 | 52 | 38 | 2 |
| M 5926 | 71 | — | 48 | — | 0 | 94 | 31 | 40 |
| M 5921 | 0 | — | 18 | — | 33 | 83 | 30 | 80 |
| JH 3 | 0 | — | 11 | 0 | 0 | 5 | 57 | 57 |

EXAMPLE 15

Acaricide activity on *Tetranychus urticae* adults and eggs.

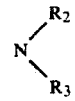

(wherein $R_2$ and $R_3$, the same or different, are H or a $C_1$–$C_5$ alkyl); or CN.

2. A compound according to claim 1, having the formula:

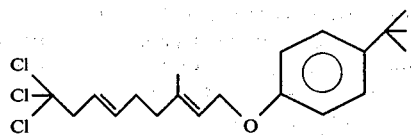

and being 4-(9,9,9-trichloro-3-methyl-nona-2,6-dienyloxy)tert.-butylbenzene.

3. A compound according to claim 1, having the formula:

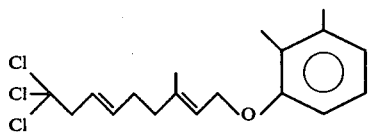

and being 1-(9,9,9-trichloro-3-methyl-nona-2,6-dienyloxy)-2,3-dimethylbenzene.

4. A compound according to claim 1, having the formula:

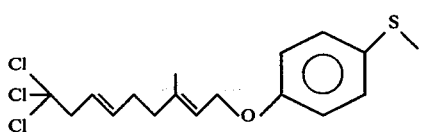

and being 4(9,9,9-trichloro-3-methyl-nona-2,6-dienyloxy)methylthio-benzene.

5. A compound according to claim 1, having the formula:

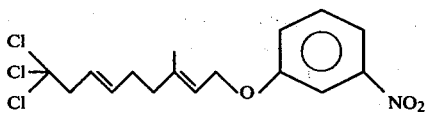

and being 3-(9,9,9-trichloro-3-methyl-nona-2,6-dienyloxy)nitrobenzene.

6. A compound according to claim 1, having the formula:

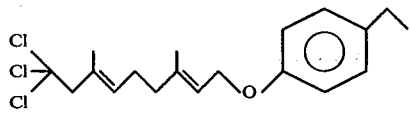

and being 4-(9,9,9-trichloro-3,7-dimethyl-nona-2,6-dienyloxy)ethylbenzene.

7. A compound according to claim 1, having the formula:

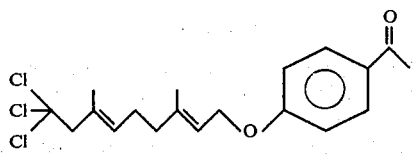

and being 4-(9,9,9-trichloro-3,7-dimethyl-nona-2,6-dienyloxy)acetophenone.

8. A compound according to claim 1, having the formula:

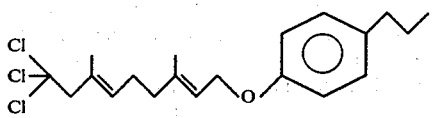

and being 4-(9,9,9-trichloro-3,7-dimethyl-nona-2,6-dienyloxy)-n-propylbenzene.

9. A compound according to claim 1, having the formula:

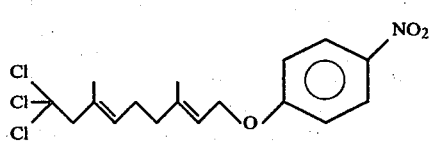

and being 4-(9,9,9-trichloro-3,7-dimethyl-nona-2,6-dienyloxy)nitrobenzene.

10. A compound according to claim 1, having the formula:

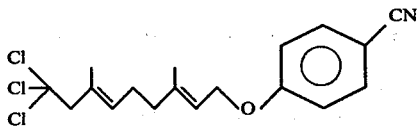

and being 4-(9,9,9-trichloro-3,7-dimethyl-nona-2,6-dienyloxy)benzonitrile.

11. An insecticide composition containing, as an essential constituent, at least one compound of formula I of claim 1, and which has both juvenile hormone activity and anti-acari activity, and a carrier for essential constituent.

12. The method of combatting noxious insects, which comprises spreading a composition comprising a carrier and the essential constituent of which is at least one compound of formula (I) of claim 1, in an amount of at least 0.01 p.p.m., or in an amount of at least 0.002 γ/insect, on the insects, the habitat thereof, the food thereof, the eggs thereof, the pupae or larvae, or the food of the pupae or larvae.

13. An insecticide composition according to claim 11, in which the carrier is water.

* * * * *